(12) United States Patent
Typpo

(10) Patent No.: US 7,071,480 B2
(45) Date of Patent: Jul. 4, 2006

(54) SENSOR WITH ALIGNMENT SELF COMPENSATION

(75) Inventor: Pekka Typpo, Cupertino, CA (US)

(73) Assignee: Voith Paper Patent GmbH, Heidenheim (DE)

( * ) Notice: Subject to any disclaimer, the term of this patent is extended or adjusted under 35 U.S.C. 154(b) by 198 days.

(21) Appl. No.: 10/461,172

(22) Filed: Jun. 13, 2003

(65) Prior Publication Data

US 2004/0251433 A1    Dec. 16, 2004

(51) Int. Cl.
    *G01N 21/86* (2006.01)
(52) U.S. Cl. ............................. 250/559.3; 250/559.29; 250/559.35; 356/400; 356/632; 73/159
(58) Field of Classification Search ............ 250/203.3, 250/559.22, 559.29, 559.35, 559.37, 559.38, 250/559.3, 208.2, 358.1, 360.1, 306, 308, 250/359.1; 73/159; 382/151, 288; 356/399, 356/400, 632; 901/46, 47; 348/94, 95
See application file for complete search history.

(56) References Cited

U.S. PATENT DOCUMENTS

| | | | | |
|---|---|---|---|---|
| 3,679,307 A * | 7/1972 | Zoot et al. | .................. | 356/3.06 |
| 4,276,480 A | 6/1981 | Watson | ........................ | 250/560 |
| 4,295,740 A * | 10/1981 | Sturges, Jr. | ............... | 356/141.3 |
| 4,329,060 A * | 5/1982 | Wilder | ........................ | 356/623 |
| 4,678,915 A | 7/1987 | Dahlquist et al. | ........ | 250/358.1 |
| 4,928,019 A * | 5/1990 | Tomikawa et al. | ........ | 250/559.3 |
| 4,936,141 A * | 6/1990 | Anderson et al. | ............. | 73/159 |
| 5,010,766 A | 4/1991 | Typpo | .......................... | 73/159 |
| 5,092,678 A * | 3/1992 | Chase et al. | ................. | 356/429 |
| 5,182,615 A * | 1/1993 | Kurosawa et al. | .......... | 356/400 |
| 5,216,258 A * | 6/1993 | McConnell | .............. | 250/559.1 |
| 5,221,985 A * | 6/1993 | Ito | .............................. | 398/129 |
| 5,227,619 A * | 7/1993 | Vilaire et al. | ............. | 250/206.2 |
| 5,233,195 A | 8/1993 | Hellstrom et al. | ........ | 250/360.1 |
| 5,289,262 A * | 2/1994 | McConnell | .................. | 356/617 |
| 5,705,804 A * | 1/1998 | Ramer et al. | ............ | 250/206.1 |
| 6,133,578 A | 10/2000 | Typpo | ..................... | 250/497.1 |

* cited by examiner

*Primary Examiner*—Thanh X. Luu
*Assistant Examiner*—Stephen Yam
(74) *Attorney, Agent, or Firm*—Taylor & Aust, P.C.

(57) ABSTRACT

A material web attribute detection system with the material web having a first side and a second side. The system includes a radiation source located proximate to the first side of the material web and emitting radiation toward the material web, and a radiation detection array located proximate to the second side of the material web and producing a plurality of signals based on the radiation detected from the radiation source. A processor is included which utilizes the plurality of signals to determine a lateral offset and a gap size of the radiation detection array relative to the radiation source. The processor can then compensate for the radiation detection array and radiation source relative misalignment using the plurality of signals, the lateral offset and the gap size.

32 Claims, 5 Drawing Sheets

SENSOR WITH ALIGNMENT SELF COMPENSATION

BACKGROUND OF THE INVENTION

1. Field of the Invention

The present invention relates to the measurement of material web characteristics, and, more particularly, to sensors used in the measurement of material web characteristics.

2. Description of the Related Art

In measuring a basis weight, moisture or thickness, or other characteristics, of a moving material web a radiation source is mounted on one side of the web material and on the other side is a receiving transducer. The source/transducer pair are then scanned in a cross direction (perpendicular to the movement or machine direction of the web material) to provide a cross direction measurement of that particular characteristic.

Any uncompensated variation in the size of the measuring gap will cause an error in the measurement. In the past, these errors were compensated either by using a separate sensor to measure the gap size, with additional references and the like or by shaping the radiation beam so that the sensitivity to alignment errors were minimized. The disadvantage of using separate sensors or additional references to measure the gap size is the increase in cost and complexity, and a corresponding decrease in reliability, associated with the additional equipment. The disadvantage in shaping the beam is the associated reduction in signal strength leads to a reduction in the signal to noise ratio.

U.S. Pat. No. 5,233,195 discloses methods and apparatus for measuring characteristics of moving webs wherein alignment insensitivity is obtained by tuning the radiation beam using concentric rings or crossed strips of material which is semi-transparent to the radiation to compensate for geometric characteristics of the radiation source/beam and the detector. U.S. Pat. No. 5,010,766 discloses error compensation for measuring gauges by the use of two pairs of eddy current sensors which are centered on a target on the opposed transducer head and which sense the pairs of edges of an aperture in the opposed transducer. U.S. Pat. No. 4,678,915 discloses a system for measuring the values of a parameter of a web of material including a head system with sensors mounted therein and a separate distance correction system. The separate distance correction system corrects the measured parameter for variations in the distance between parts of the head system using a coil circuit. U.S. Pat. No. 4,276,480 discloses a sensor response indicative of a distance which can be related to a thickness property of a material by a procedure that includes establishing a reference position, such as to a support, and locating the material precisely in a predetermined spatial relation to the reference position.

What is needed in the art is a sensor which is insensitive to both lateral and vertical misalignment between the radiation source and receiver and which does not require additional detecting elements, references or beam shaping.

SUMMARY OF THE INVENTION

The present invention provides a sensor for detecting web qualities which is self compensating with respect to the sensor alignment.

The invention comprises, in one form thereof, a material web attribute detection system with the material web having a first side and a second side. The system includes a radiation source located proximate to the first side of the material web and emitting radiation toward the material web, and a radiation detection array located proximate to the second side of the material web and producing a plurality of signals based on the radiation detected from the radiation source. A processor is included which utilizes the plurality of signals to determine a lateral offset and a gap size of the radiation detection array relative to the radiation source. The processor can then compensate for the radiation detection array and radiation source relative misalignment using the plurality of signals, the lateral offset and the gap size.

An advantage of the present invention is that it provides a method and apparatus to compensate sensors for misalignment over a wide range.

Another advantage of the present invention is that the sensor can be optimized mathematically with greater accuracy than what has been possible with the prior art.

Yet another advantage of the present invention is that it does not require additional sensor elements for alignment compensation.

A further advantage of the present invention is that it does not require additional reference elements for alignment compensation.

A further advantage of the present invention is that it does not require radiation beam shaping for alignment compensation.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
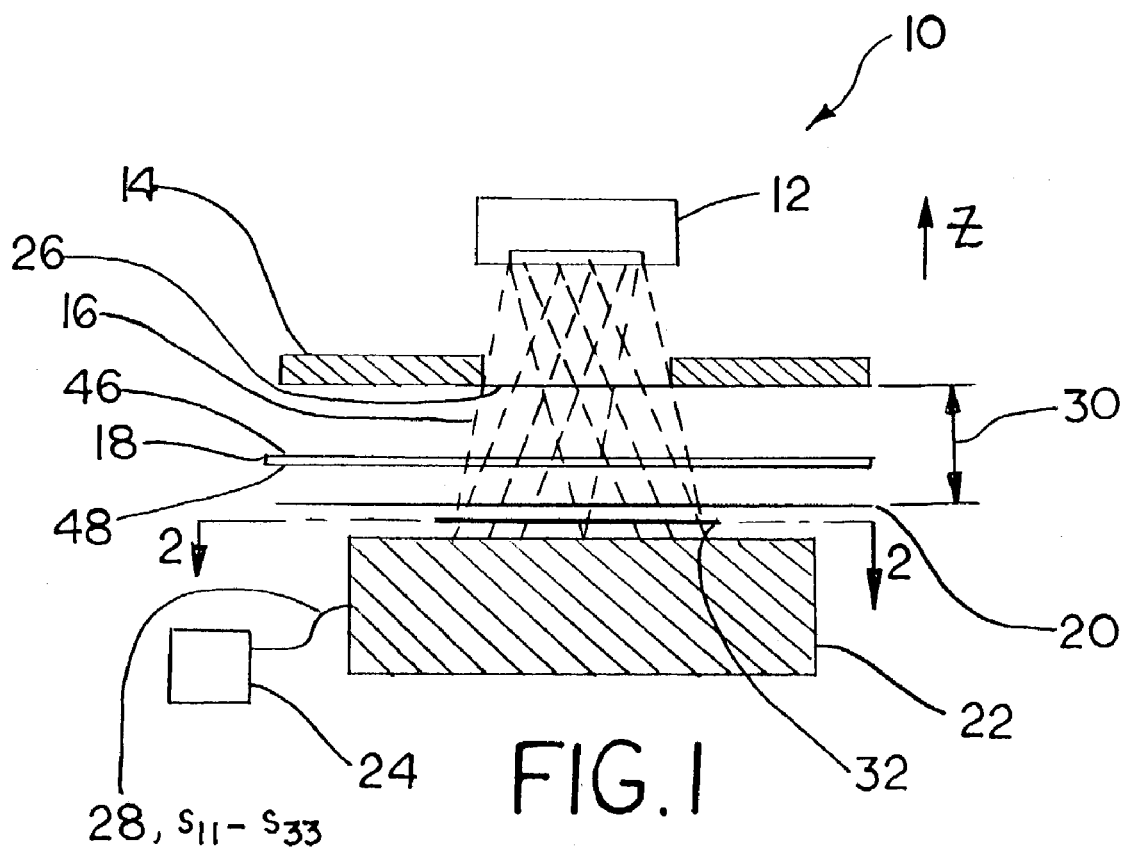
FIG. 1 is a schematic side view of an embodiment of the material web attribute detection system of the present invention.
Figure 2:
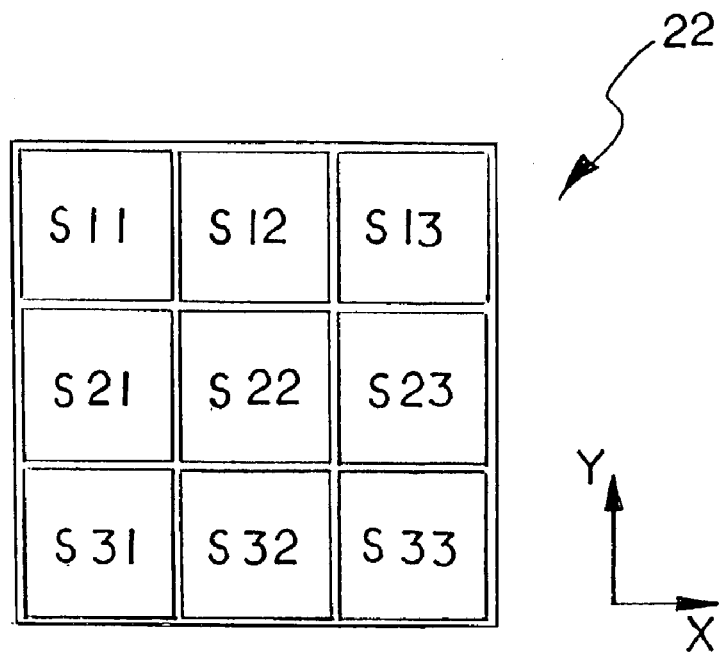
FIG. 2 is a schematic plan view of an embodiment of a sensor with alignment self compensation of FIG. 1 taken along section line 2—2.

Referring now to the drawings, and more particularly to FIG. 1, there is shown an embodiment of a material web attribute detection system 10 of the present invention including radiation source 12, source aperture and window 14, radiation beam 16, material web 18, receiver window 20, detector or sensor array 22 and processor 24.

Radiation source 12 generates radioactive particles and/or electromagnetic energy. Radiation source 12 can be surrounded by a radiation absorbing or reflecting material with an opening on one side to thereby mainly emit radiation from one side of radiation source 12. Radiation source 12 can, for example, emit primarily beta particles or x-rays but is not limited to such particle or energy emission. Alternatively, radiation source 12 can emit in any range of the electromagnetic spectrum including radio, microwave, infrared, ultraviolet, gamma ray and cosmic ray spectral ranges, and higher energy atomic and subatomic particles. Source aperture and window 14 includes aperture 26 through which radiation emitted by radiation source 12 can pass through. Aperture 26 can be closed and opened under command of processor 24 or another control mechanism (not shown). Source aperture and window 14 is generally positionally and angularly fixed with respect to radiation source 12. Alternatively, source aperture and window 14 are adjustable.

Material web 18 is suspended between detector array 22 and the combination radiation source 12 and source aperture and window 14. Gap 30, between source aperture and window 14 and detector window 20, is sufficiently wide that material web 18 does not touch either source aperture 14 or detector window 20. Material web 18 is typically a moving web of material such as paper, cardboard or a plastic. Material web has a machine direction (MD) and a cross-machine direction (CD).

Figure 5:
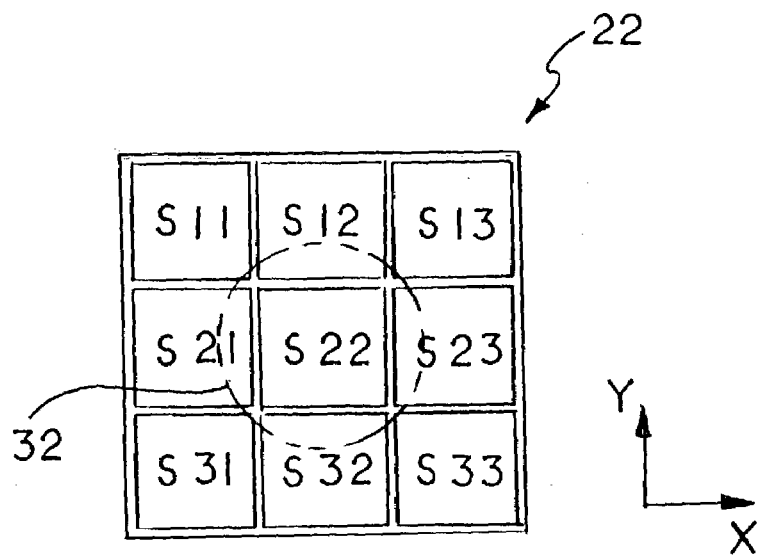
FIG. 5 is a schematic plan view of the sensor of FIG. 1 taken along section line 2—2 and showing a projection of a radiation beam in substantial alignment with the sensor.

Detector array or array sensor 22 is connected to processor 24 by way of communication link 28. Detector array 22 includes receiver window 20, and can also include an aperture which can be controlled similarly to aperture 26, and multiple individual detector or sensor elements arrayed in a geometric pattern such as sensor elements S11, S12, S13, S21, S22, S23, S31, S32, and S33. Detector array 22 communicates to processor 24 signals $s_{11}$, $s_{12}$, $s_{13}$ $s_{21}$, $s_{22}$, $s_{23}$, $s_{31}$, $s_{32}$ and $s_{33}$ indicative of the amount of radiation detected by each of sensor elements S11, S12, S13, S21, S22, S23, S31, S32, and S33, respectively. Ideally, detector array 22 is positioned in substantial alignment with radiation source 12 to thereby centrally locate sensor S22, so as to be substantially centered in radiation beam 16 as shown in FIGS. 1 and 5. The peak intensity of radiation beam 16, as represented in FIG. 5, is substantially directed toward sensor S22. While a substantial alignment of radiation beam 16 is desired, the present invention determines and compensates for any misalignment. Receiver window 20 is generally positionally and angularly fixed with respect to detector array 22. Alternatively, receiver window 20 is adjustable.

Due to mechanical imperfections of the transverse mechanisms, such as carriages 42 and 44 (FIG. 4), or the respective mountings and respective housings of radiation source 12 and detector array 22, and the sensitivity of the measuring transducers 12, 22 themselves, a constant positional relationship both in a Z direction, which is perpendicular to the moving sheet, and X, Y directions which are in the plane of the moving sheet are not always maintained. Other causes of misalignment can be angular displacement or positional displacement of radiation source 12 and/or detector array 22 resulting from tolerance stackup, original alignment errors and/or subsequent alignment errors resulting from machine vibration or other operational conditions causing radiation source 12 and/or detector array 22, to move or be misaligned, either angularly or positionally, with respect to each other.

Figure 6:
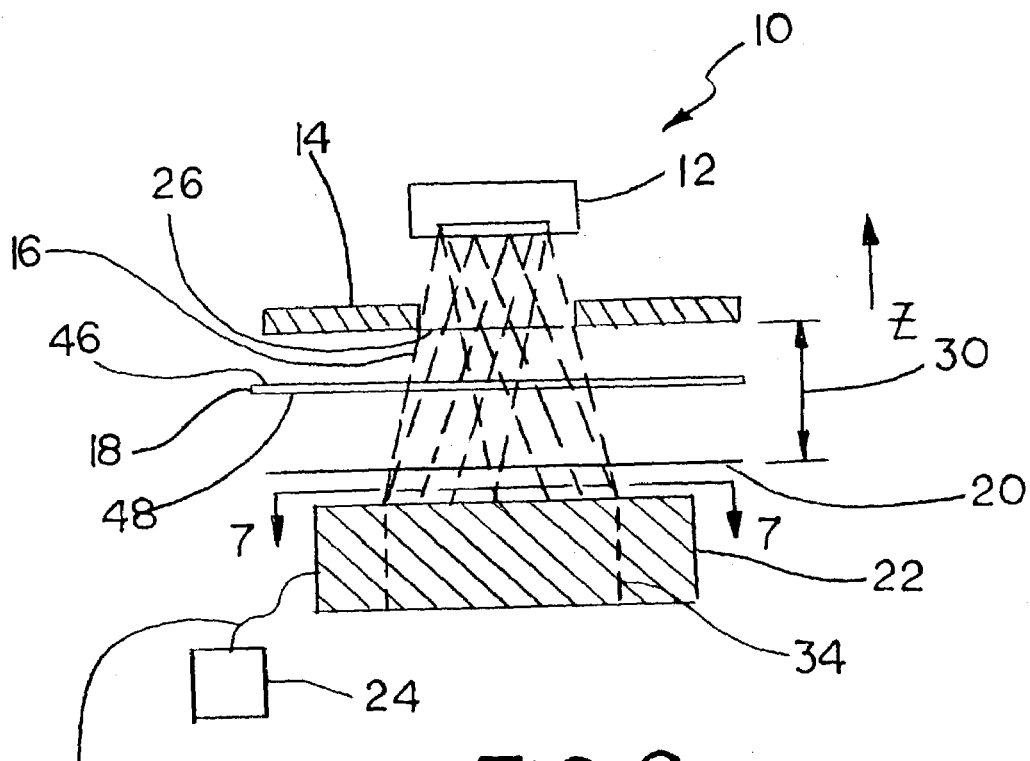
FIG. 6 is a schematic side view of an embodiment of the material web attribute detection system showing gap (z direction) misalignment between a radiation source and a detector array.
Figure 7:
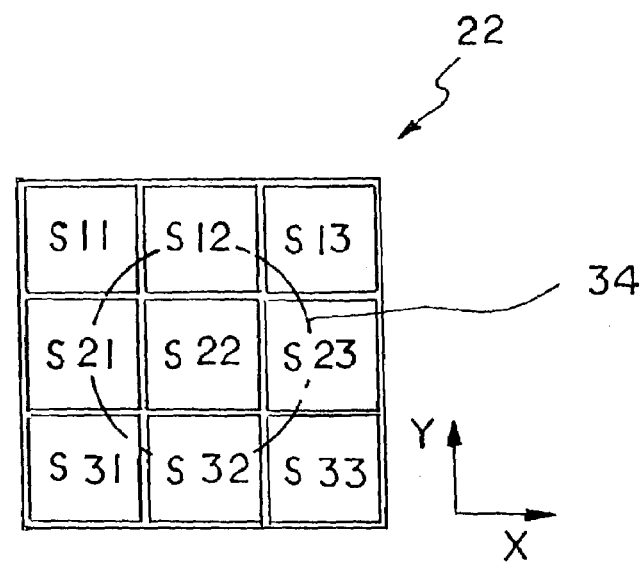
FIG. 7 is a schematic plan view of the sensor of FIG. 6 taken along section line 7—7 and showing the effect of gap misalignment on the projection of the radiation beam on the sensor.
Figure 8:
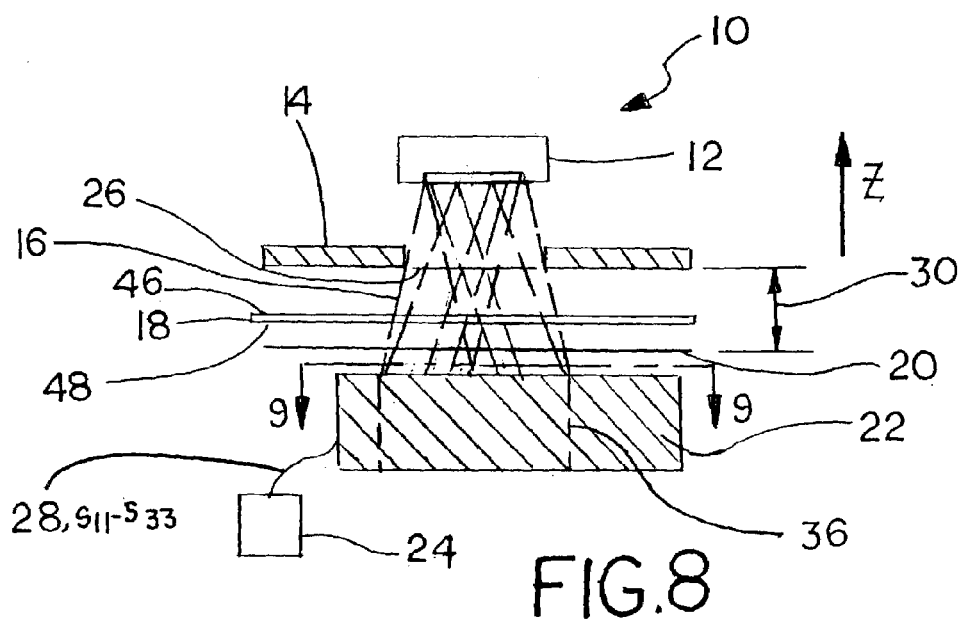
FIG. 8 is a schematic side view of an embodiment of the material web attribute detection system showing lateral (x,y direction) misalignment between the radiation source and detector array.
Figure 9:
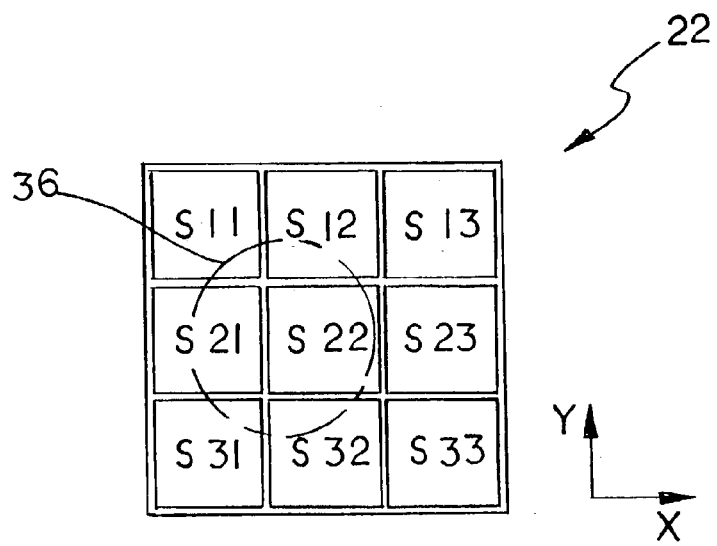
FIG. 9 is a schematic plan view of the sensor of FIG. 8 taken along section line 9—9 and showing the effect of lateral misalignment on the projection of the radiation beam on the sensor.

FIG. 1 shows radiation source 12 in substantial relative alignment with detector array 22. FIG. 5 shows nominal beam projection 32 on detector array 22 resulting from the alignment shown in FIG. 1. FIG. 6 shows radiation source 12 in Z direction, or gap, misalignment with detector array 22. FIG. 7 shows beam projection 34 broadened on detector array 22 with gap misalignment resulting from the misalignment shown in FIG. 6. FIG. 8 shows radiation source 12 in lateral, or X,Y direction misalignment with detector array 22. FIG. 9 shows beam projection 36 offset on detector array 22 resulting from the misalignment shown in FIG. 8.

Radiation beam 16 (wave, particle or combination thereof), from radiation source 12, propagates through source aperture and window 14, material web 18 and detector window 20 to arrive at detector array 22. Detector window 20 is substantially transparent to the radiation and may include an antireflective coating similar to source aperture and window 14. Information or signals $S_{11}$, $S_{12}$, $S_{13}$ $S_{21}$, $S_{22}$, $S_{23}$, $S_{31}$, $S_{32}$ and $S_{33}$ from detector array 22 to processor 24 can be in the form of an analog signal or digital information, which can be in the form of a digital count that is representative of the amount of radiation detected by each of sensors S11–S33 from radiation source 12.

Processor 24 communicates with detector array 22 by way of communications link 28. Information and/or signals $s_{11}$–$s_{33}$ from detector array 22 are received by processor 24 and such information or signals are processed to calculate a lateral position (x,y) of detector array 22 relative to source 12 in an X and Y direction using the formulas:

$$x=(s_{12}-s_{32})/(s_{12}+s_{32}) \text{ and} \quad (1)$$

$$y=(s_{21}-s_{23})/(s_{21}+s_{23}). \quad (2)$$

A gap 30 size (z) between source aperture and window 14 detector window 28 is calculated using the formula:

$$z=[(s_{12}+s_{23}+s_{32}+s_{21})/\{S_{22}*[1+F*(x^2+y^2)]\} \quad (3)$$

where F=a calibration constant.

A corrected signal or value s can be calculated for the overall detector array 22 response, and compensating for lateral position and gap size misalignment of the detector array 22 using the formula:

$$s=(s_{11}+s_{12}+s_{13}+s_{21}+s_{22}+s_{23}+s_{31}+s_{32}+s_{33})* [1+A*x+B*y+C*(x^2+y^2)+D*x+E*z^2] \quad (4)$$

where:
A=a misalignment calibration constant
B=a misalignment calibration constant
C=a misalignment calibration constant
D=a misalignment calibration constant and
E=a misalignment calibration constant.

Radiation beam 16 is emitted from radiation source 12 through aperture 14 impacting material web 18 and at least some of the particles or radiation from radiation source 12 reaches detector array 22. Radiation beam 16 may be in the form of an energy and/or particle beam, or combination thereof, from radiation source 12, and is somewhat distorted and or attenuated by its encounter with material web 18. The amount of and manner of the distortion and attenuation of radiation beam 16, as it interacts with material web 18, is dependent on many factors including the composition of material web 18, the variablility of material web 18, the relative thickness of material web 18, basis weight and moisture of material web 18, the Z positioning of material web 18 and the size of gap 30. Corrected signal or value s provides an indication of web quality compensated for radiation source 12 and detector array 22 misalignments.

Figure 3:
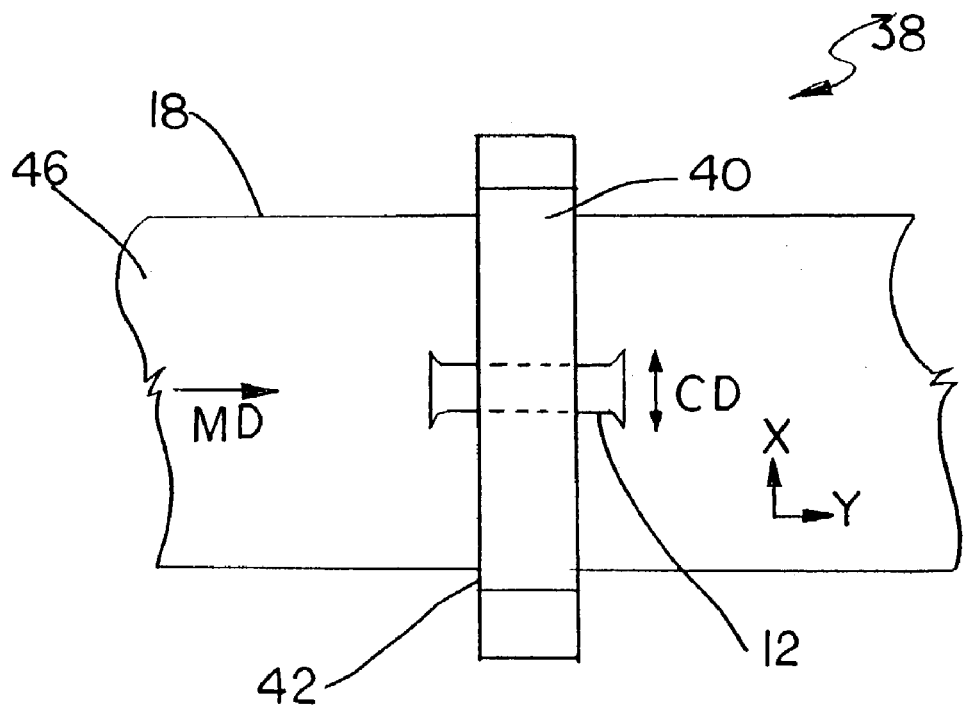
FIG. 3 is a schematic plan view of an embodiment of a material web attribute gauge of the present invention.
Figure 4:
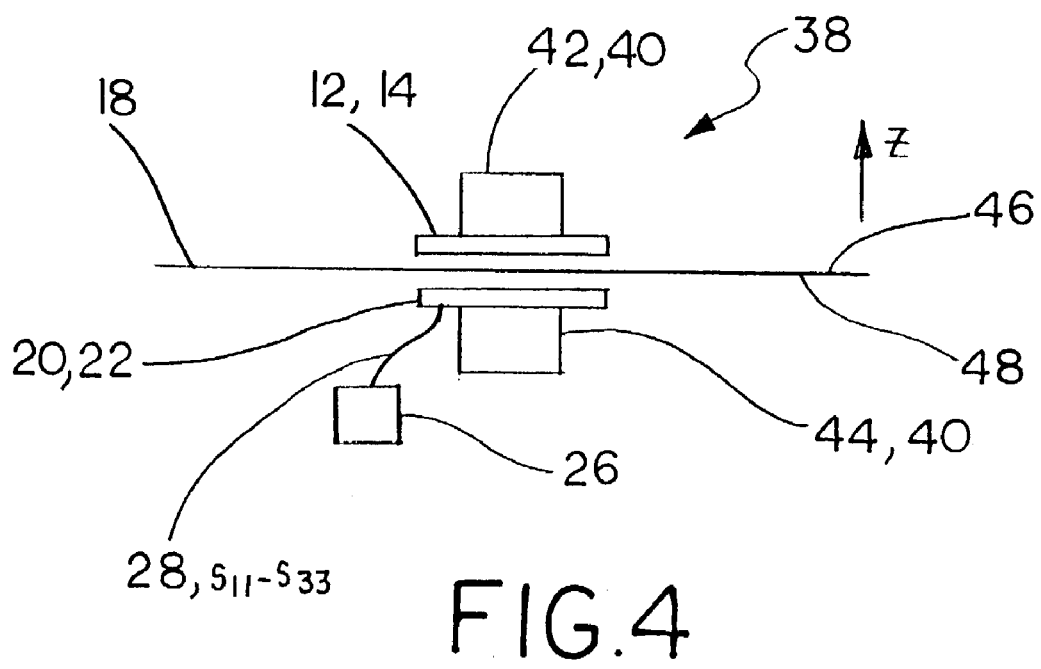
FIG. 4 is a schematic side view of the material web attribute gauge of FIG. 3.

FIGS. 3 and 4 illustrate material web attribute gauge 38 including transport mechanism 40 having first carriage 42 and second carriage 44, first carriage 42 and second carriage 44 being connected such that movement of first carriage 42 and second carriage 44 is coordinated to keep first carriage 42 and second carriage 44 in substantial alignment with each other. First carriage 42 is located proximate to first side 46 of material web 18; second carriage 44 is located proximate to second side 48 of material web 18. Radiation source 16 and source aperture and window 14 are positioned on first carriage 42. Detector array 22 and receiver window 20 are positioned on second carriage 44. Transport mechanism 40 scans radiation source 16, source aperture and window 14, detector array 22 and receiver window 20 in a cross-machine direction. Detector array 22 produces a plurality of signals $s_{11}$–$s_{33}$, as previously described, as to the amount of radiation received from radiation source 16. Processor 24 utilizes said a plurality of signals to determine a lateral offset and gap size of said radiation detection array relative to said radiation source, and to calculate corrected signal or value s, all as previously described.

Figure 10:
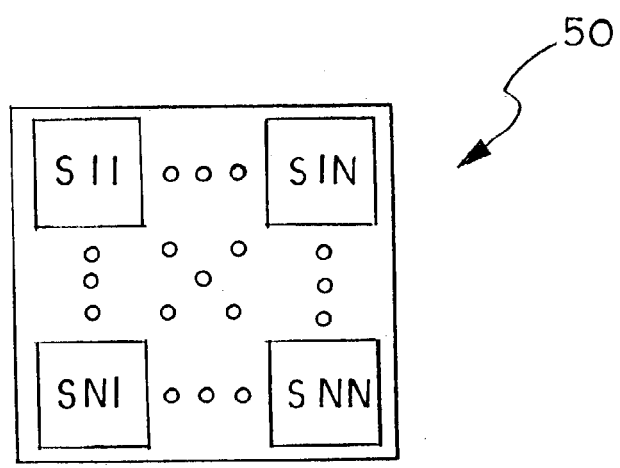
FIG. 10 is a schematic plan view of an embodiment of a generalized sensor with alignment self compensation showing an N×N array of sensor elements.

FIG. 10 illustrates a generalized N×N detector array 50 where N is an integer greater than 3. Detector array 50 can be used in a manner similar to detector array 22 with appropriate modifications to equations (1)–(4).

In use, material web attribute detection system 10 is operated by providing radiation source 12 and array sensor 22 with a plurality of sensor elements S11–S33. A plurality of signals $s_{11}$–$s_{33}$ is produced in the plurality of sensor elements S11–S33. A lateral position (x,y) of sensor 22 relative to radiation source 12 is calculated using the plurality of signals $S_{11}$–$s_{33}$ as previously described. Gap size 30 of sensor 22 relative to radiation source 12 is calculated using the plurality of signals $s_{11}$–$s_{33}$ as previously described. Both the lateral position and the gap size misalignment of sensor 22 is compensated for using the calculated lateral position and the calculated gap size. A corrected signal or value s resulting from the real time compensation of sensor 22 is an indicator of a quality or a characteristic for material web 18 with the effects of a relative misalignment of radiation source 12 and array sensor 22 removed.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of operating a sensor to detect at least one attribute of a moving material web, comprising the steps of:
   providing a radiation source and a sensor with a plurality of sensor elements;
   producing a plurality of signals in said plurality of sensor elements by irradiating the moving material web with a radiation energy of said radiation source, said sensor detecting at least some of said radiation energy that has penetrated the moving material web;
   measuring at least one attribute of the moving material web with said sensor; and
   calculating a lateral position of said sensor relative to said radiation source using said plurality of signals.

2. The method of claim 1, further including a step of calculating a gap size of said sensor relative to said radiation source using said plurality of signals.

3. The method of claim 2, further including a step of compensating said at least one attribute for both said lateral position and said gap size of said sensor using said calculated lateral position and said calculated gap size.

4. The method of claim 3, wherein said sensor is a 3×3 array sensor with sensor elements S11, S12, S13, S21, S22, S23, S31, S32, S33.

5. The method of claim 4, wherein said plurality of signals correspond to signals $s_{11}$, $s_{12}$, $s_{13}$ $s_{21}$, $s_{22}$, $s_{23}$, $s_{32}$, $s_{33}$ in corresponding said sensor elements S11, S12, S13, S21, S22, S23, S31, S32, S33, respectively.

6. The method of claim 5, wherein said lateral position of said sensor is calculated with the formulas:

$$x=(s_{12}-s_{32})/(s_{12}+s_{32}) \text{ and}$$

$$y=(s_{21}-s_{23})/(s_{21}+s_{23}).$$

7. The method of claim 1, wherein said array sensor is a N×N array with N×N elements where N is an integer greater than 3.

8. The method of claim 1, wherein the material web is one of a paper web and a cardboard web.

9. A method of operating a sensor, comprising the steps of:
providing a radiation source and a sensor with a plurality of sensor elements, said sensor is a 3×3 array sensor with sensor elements S11, S12, S13, S21, S22, S23, S31, S32, S33;
producing a plurality of signals in said plurality of sensor elements, said plurality of signals correspond to signals $s_{11}$, $s_{12}$, $s_{13}$ $s_{21}$, $s_{22}$, $s_{23}$, $s_{31}$, $s_{32}$, $s_{33}$ in corresponding said sensor elements S11, S12, S13, S21, S22, S23, S31, S32, S33, respectively:
calculating a lateral position of said sensor relative to said radiation source using said plurality of signals, said lateral position of said sensor is calculated with the formulas:

$$x=(s_{12}-s_{32})/(s_{12}+s_{32}) \text{ and}$$

$$y=(s_{21}-s_{23})/(s_{21}+s_{23});$$

calculating a gap size of said sensor relative to said radiation source using said plurality of signals, wherein said gap size of said sensor is calculated with the formula:

$$z=(s_{12}+s_{23}+s_{32}+s_{21})/\{s_{22}*[1+F*(x^2+y^2)]\}$$

where F=calibration constant; and
compensating for both said lateral position and said gap size of said sensor using said calculated lateral position and said calculated gap size.

10. The method of claim 9, wherein said compensating step is calculated using the formula:

$$s=(s_{11}+s_{12}+s_{13}+s_{21}+s_{22}+s_{23}+s_{31}s+s_{32}+s_{33})*[1+A*x+B*y+C*(x^2+y^2)+D*z+E*z^2]$$

where:
A=a misalignment calibration constant
B=a misalignment calibration constant
C=a misalignment calibration constant
D=a misalignment calibration constant and
E=a misalignment calibration constant.

11. A moving material web attribute detection system, the moving material web having a first side and a second side, the system comprising:
a radiation source located proximate to the first side of the moving material web, said radiation source emitting radiation toward the moving material web;
a detector array located proximate to the second side of the moving material web, said radiation detection array producing a plurality of signals based on a detected radiation from said radiation source that has penetrated the moving material web; and
a processor utilizing said plurality of signals to determine at least one attribute of the moving material web and a lateral position of said detector array relative to said radiation source.

12. The system of claim 11, wherein said processor utilizes said plurality of signals to determine a gap size of said detector array relative to said radiation source.

13. The system of claim 12, wherein said processor utilizes said plurality of signals to compensate said at least one attribute for both said lateral position and said gap size.

14. The system of claim 13, wherein said detector array is a 3×3 detector array with detector elements S11, S12, S13, S21, S22, S23, S31, S32, S33.

15. The system of claim 14, wherein said plurality of signals correspond to signals $s_{11}$, $s_{12}$, $s_{13}$ $s_{21}$, $s_{22}$, $s_{23}$, $s_{31}$, $s_{32}$, $s_{33}$ provided by corresponding said sensor elements S11, S12, S13, S21, S22, S23, S31, S32, S33, respectively.

16. The system of claim 15, wherein said lateral position is calculated with the formulas:

$$x=(s_{12}-s_{32})/(s_{12}+s_{32}) \text{ and}$$

$$y=(s_{21}-s_{23})/(s_{21}+s_{23}).$$

17. The system of claim 11, wherein said detector array is a N×N array with N×N elements where N is an integer greater than 3.

18. The system of claim 11, wherein both said detector array and said radiation source are scanned in a cross-machine direction of the material web.

19. The system of claim 11, wherein the material web is one of a paper web and a cardboard web.

20. A material web attribute detection system, the material web having a first side and a second side, the system comprising:
a radiation source located proximate to the first side of the material web, said radiation source emitting radiation toward the material web;
a detector array located proximate to the second side of the material web, said radiation detection array producing a plurality of signals based on a detected radiation from said radiation source, said detector array is a 3×3 detector array with detector elements S11, S12, S13, S21, S22, S23, S31, S32, S33, said plurality of signals correspond to signals $s_{11}$, $s_{12}$, $s_{13}$ $s_{21}$, $s_{22}$, $s_{23}$, $s_{31}$, $s_{32}$, $s_{33}$ provided by corresponding said sensor elements S11, S12, S13, S21, S22, S23, S31, S32, S33, respectively; and
a processor utilizing said plurality of signals to determine a lateral position of said detector array relative to said radiation source, said processor utilizing said plurality of signals to determine a gap size of said detector array relative to said radiation source, said processor utilizing said plurality of signals to compensate for both said lateral position and said gap size, wherein said lateral position is calculated with the formulas:

$$x=(s_{12}-s_{32})/(s_{12}+s_{32}) \text{ and}$$

$$y=(s_{21}-s_{23})/(s_{21}+s_{23}),$$

wherein said gap size is calculated with the formula:

$$z=(s_{12}+s_{23}+s_{32}+s_{21})/\{s_{22}*[1+F*(x^2+y^2)]\} \text{ and}$$

where F=a calibration constant.

21. The system of claim 20, wherein said compensating step is calculated using the formula:

$$s=(s_{11}+s_{12}+s_{13}+s_{21}s+s_{22}+s_{23}+s_{31}s+s_{32}+s_{33})*[1+A*x+B*y+C*(x^2+y^2)+D*z+E*z^2]$$

where:
A=a misalignment calibration constant
B=a misalignment calibration constant
C=a misalignment calibration constant
D=a misalignment calibration constant and
E=a misalignment calibration constant.

22. A moving material web attribute gauge, the moving material web having a first side and a second side, comprising:

a transport mechanism including a first carriage and a second carriage, said first carriage and said second carriage being connected such that movement of said first carriage and said second carriage is coordinated to keep said first carriage in substantial alignment with said second carriage, said first carriage located proximate to the first side of the moving material web, said second carriage located proximate to the second side of the moving material web;

a radiation source positioned on said first carriage, said radiation source emitting radiation toward the moving material web;

a detector array positioned on said second carriage, said radiation detection array producing a plurality of signals based on a detected radiation from said radiation source that has penetrated the moving material web; and a processor utilizing said plurality of signals to determine at least one attribute of the moving material web and a lateral offset of said detector array relative to said radiation source.

23. The gauge of claim 22, wherein said processor utilizes said plurality of signals to determine a gap size of said detector array relative to said radiation source.

24. The gauge of claim 23, wherein said processor utilizes said plurality of signals to compensate said at least one attribute for both said lateral position and said gap size.

25. The gauge of claim 24, wherein said detector array is a 3×3 detector array with detector elements S11, S12, S13, S21, S22, S23, S31, S32, S33.

26. The gauge of claim 25, wherein said plurality of signals correspond to signals $s_{11}$, $s_{12}$, $s_{13}$ $s_{21}$, $s_{22}$, $s_{23}$, $s_{31}$, $s_{32}$, $s_{33}$ provided by corresponding said sensor elements S11, S12, S13, S21, S22, S23, S31, S32, S33, respectively.

27. The gauge of claim 26, wherein said lateral position is calculated with the formulas:

$$x=(s_{12}-s_{32})/(s_{12}+s_{32}) \text{ and}$$

$$y=(s_{21}-s_{23})/(s_{21}+s_{23}).$$

28. The gauge of claim 22, wherein said detector array is a N×N array with N×N elements where N is an integer greater than 3.

29. The gauge of claim 22, wherein both said detector array and said radiation source are scanned in a cross-machine direction of the material web.

30. The gauge of claim 22, wherein the material web is one of a paper web and a cardboard web.

31. A material web attribute gauge, the material web having a first side and a second side, comprising:

a transport mechanism including a first carriage and a second carriage, said first carriage and said second carriage being connected such that movement of said first carriage and said second carriage is coordinated to keep said first carriage in substantial alignment with said second carriage, said first carriage located proximate to the first side of the material web, said second carriage located proximate to the second side of the material web;

a radiation source positioned on said first carriage, said radiation source emitting radiation toward the material web;

a detector array positioned on said second carriage, said radiation detection array producing a plurality of signals based on a detected radiation from said radiation source, said detector array is a 3×3 detector array with detector elements S11, S12, S13, S21, S22, S23, S31, S32, S33, said plurality of signals correspond to signals $s_{11}$, $s_{12}$, $s_{13}$ $s_{21}$, $s_{22}$, $s_{23}$, $s_{31}$, $s_{32}$, $s_{33}$ provided by corresponding said sensor elements S11, S12, S13, S21, S22, S23, S31, S32, S33, respectively; and a processor utilizing said plurality of signals to determine a lateral offset of said detector array relative to said radiation source, said processor utilizing said plurality of signals to determine a gap size of said detector array relative to said radiation source, said processor utilizing said plurality of signals to compensate for both said lateral position and said gap size, wherein said lateral position is calculated with the formulas:

$$x=(s_{12}-s_{32})/(s_{12}+s_{32}) \text{ and}$$

$$y=(s_{21}-s_{23})/(s_{21}+s_{23}),$$

wherein said gap size is calculated with the formula:

$$z=(s_{12}+s_{23}+s_{32}+s_{21})/\{s_{22}*[1+F*(x^2+y^2)]\} \text{ and}$$

where F=a calibration constant.

32. The gauge of claim 31, wherein said compensating step is calculated using the formula:

$$s=(s_{11}+s_{12}+s_{13}+s_{21}+s_{22}+s_{23}+s_{31}+s_{32}+s_{33})*[1+A*x+B*y+C*(x^2+y^2)+D*z+E*z^2]$$

where:

A=a misalignment calibration constant
B=a misalignment calibration constant
C=a misalignment calibration constant
D=a misalignment calibration constant and
E=a misalignment calibration constant.

* * * * *

UNITED STATES PATENT AND TRADEMARK OFFICE
CERTIFICATE OF CORRECTION

| | | |
|---|---|---|
| PATENT NO. | : 7,071,480 B2 | Page 1 of 1 |
| APPLICATION NO. | : 10/461172 | |
| DATED | : July 4, 2006 | |
| INVENTOR(S) | : Typpo | |

It is certified that error appears in the above-identified patent and that said Letters Patent is hereby corrected as shown below:

COLUMN 5

At line 18, in formula (4), please delete "$s=(s_{11}+s_{12}+s_{13}+s_{21}+s_{22}+s_{23}+s_{31}+s_{32}+s_{33})*[1+A*x+B*y+C*(x^2+y^2)+D*x+E*z^2]$", and substitute therefore --$s=(s_{11}+s_{12}+s_{13}+s_{21}+s_{22}+s_{23}+s_{31}+s_{32}+s_{33})*[1+A*x+B*y+C*(x^2+y^2)+D*z+E*z^2]$--.

Signed and Sealed this

Fifteenth Day of May, 2007

JON W. DUDAS
*Director of the United States Patent and Trademark Office*